US012329727B2

(12) United States Patent
Marchant et al.

(10) Patent No.: US 12,329,727 B2
(45) Date of Patent: Jun. 17, 2025

(54) USE OF SALMETEROL AS AN ANTI-CORONAVIRAL AGENT

(71) Applicant: The Medical College of Wisconsin, Inc., Milwaukee, WI (US)

(72) Inventors: Jonathan Stephen Marchant, Brookfield, WI (US); Tom Paul Aufderheide, Wauwatosa, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 487 days.

(21) Appl. No.: 17/920,611

(22) PCT Filed: Apr. 21, 2021

(86) PCT No.: PCT/US2021/028399
§ 371 (c)(1),
(2) Date: Oct. 21, 2022

(87) PCT Pub. No.: WO2021/216710
PCT Pub. Date: Oct. 28, 2021

(65) Prior Publication Data
US 2023/0149327 A1 May 18, 2023

Related U.S. Application Data

(60) Provisional application No. 63/015,307, filed on Apr. 24, 2020.

(51) Int. Cl.
*A61K 31/137* (2006.01)
*A61K 45/06* (2006.01)
*A61P 31/14* (2006.01)

(52) U.S. Cl.
CPC ............ *A61K 31/137* (2013.01); *A61K 45/06* (2013.01); *A61P 31/14* (2018.01)

(58) Field of Classification Search
CPC .... A61K 31/137; A61K 45/06; A61K 9/0043; A61P 31/14
See application file for complete search history.

(56) References Cited

U.S. PATENT DOCUMENTS

| 6,303,103 | B1 | 10/2001 | Akehurst et al. |
| 7,090,831 | B1 | 8/2006 | Bonvoisin et al. |
| 2004/0050960 | A1 | 3/2004 | Godfrey et al. |
| 2005/0042174 | A1 | 2/2005 | Nilsson et al. |
| 2013/0203715 | A1 | 8/2013 | Hava et al. |
| 2017/0304564 | A1 | 10/2017 | DeHaan et al. |

FOREIGN PATENT DOCUMENTS

WO 2012107765 A2 8/2012

OTHER PUBLICATIONS

International Search Report issued for PCT/US2021/028399 dated Jul. 14, 2021.
International Preliminary Report on Patentability issued for PCT/US2021/028399 dated Jul. 14, 2021.
Britton, M. G., et al., "A twelve month comparison of salmeterol with salbutamol in asthmatic patients." European Study Group. Eur. Respir. (1992) J. 5, 1062-1067.
D'Alonzo, G. E., et al., "Salmeterol xinafoate as maintenance therapy compared with albuterol in patients with asthma." JAMA (1994) 271, 1412-1416.
Devalia, J. L., et al., "The effects of salmeterol and salbutamol on ciliary beat frequency of cultured human bronchial epithelial cells, in vitro." Pulm. Pharmacol. (1992) 5, 257-263.
Gunaratne, G. S., et al., "Essential requirement for Jupiter Microtubule Associated Homolog 2 in NAADP-evoked Ca2+ signaling and SARS-COV-2 infectivity." Science Signaling (in press) (2021) vol. 14; Issue 675; DOI: 10.1126/scisignal.abd5605.
Gunaratne, G. S., et al., "NAADP-dependent Ca(2+) signaling regulates Middle East respiratory syndrome-coronavirus pseudovirus translocation through the endolysosomal system." Cell Calcium (2018) 75, 30-41.
Gunaratne, G. S., et al., "A screening campaign in sea urchin egg homogenate as a platform for discovering modulators of NAADP-dependent Ca(2+) signaling in human cells." Cell Calcium (2018) 75, 42-52.
Li, X., et al., "An antiinflammatory effect of salmeterol, a long-acting beta(2) agonist, assessed in airway biopsies and bronchoalveolar lavage in asthma." Am. J. Respir. Crit. Care Med. (1999) 160, 1493-1499.
https://www.cdc.gov/coronavirus/2019-ncov/your-health/treatments-for-severe-illness.html?CDC_AA_refVal=https%3A%2F%2Fwww.cdc.gov%2Fcoronavirus%2F2019-ncov%2Fhcp%2Ftherapeutic-options.html.
Liu et al. "Research and development on therapeutic agents and vaccines for COVID-19 and related human coronavirus diseases," ACS Central Science (2020) 6, 315-331.
Maris, N. A., et al., "Antiinflammatory effects of salmeterol after inhalation of lipopolysaccharide by healthy volunteers." Am. J. Respir. Crit. Care Med. (2005) 172, 878-884.
Nelson, H. S., "Advair: combination treatment with fluticasone propionate/salmeterol in the treatment of asthma." J. Allergy Clin. Immunol. (2001) 107, 398-416.
Ou, X., et al., "Characterization of spike glycoprotein of SARS-COV-2 on virus entry and its immune cross-reactivity with SARS-COV." Nature Communications (2020) 11, 1620.
Penny, C. J., et al., "Mining of Ebola virus entry inhibitors identifies approved drugs as two-pore channel pore blockers." Biochim Biophys Acta Mol Cell Res (2019) 1866, 1151-1161.
Pearlman, D. S., et al., "A comparison of salmeterol with albuterol in the treatment of mild-to-moderate asthma." N. Engl. J. Med. (1992) 327, 1420-1425.
Sakurai, et al., "Ebola virus. Two-pore channels control Ebola virus host cell entry and are drug targets for disease treatment." Science (2015) 347, 995-998.

(Continued)

*Primary Examiner* — Umamaheswari Ramachandran
(74) *Attorney, Agent, or Firm* — Quarles & Brady LLP

(57) ABSTRACT

Described herein are methods for treating COVID-19 or preventing COVID-19 in a subject exposed to SARS-CoV-2 by administering to the subject a therapeutically effective amount of salmeterol or the pharmaceutically acceptable salt thereof.

18 Claims, 14 Drawing Sheets

(56) References Cited

OTHER PUBLICATIONS

Shang, J., et al., "Cell entry mechanisms of SARS-COV-2." Proc. Natl. Acad. Sci. U. S. A. (2020) 117, 11727-11734.
Taylor, D. R., et al., "Asthma control during long-term treatment with regular inhaled salbutamol and salmeterol." Thorax (1998) 53, 744-752.
Trott, O., et al., "AutoDock Vina: improving the speed and accuracy of docking with a new scoring function, efficient optimization, and multithreading." Journal of computational chemistry (2010) 31, 455-461.

FIG. 3 (continued)

cADPR

FIG. 3 (continued)

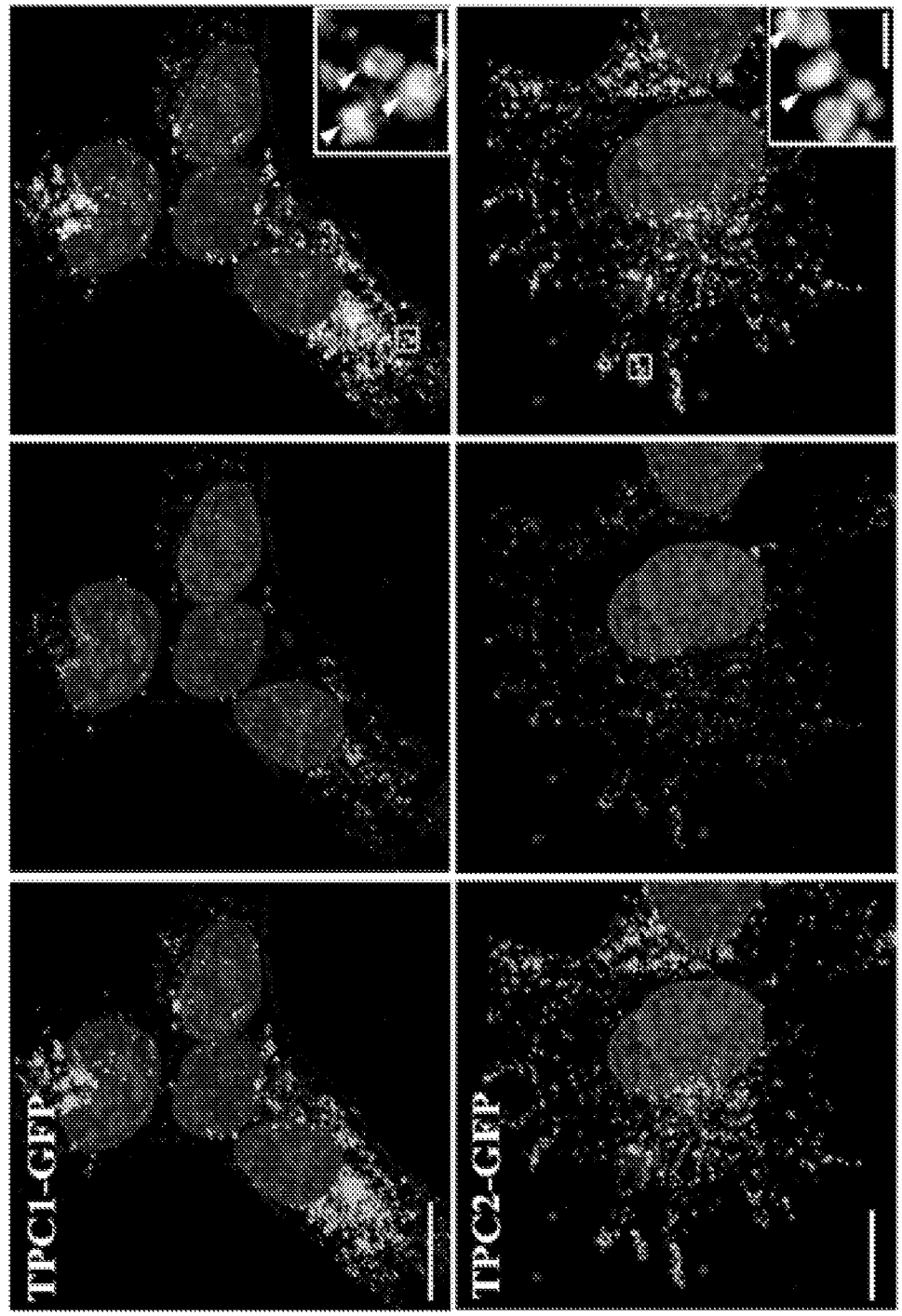

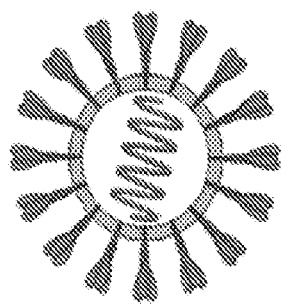
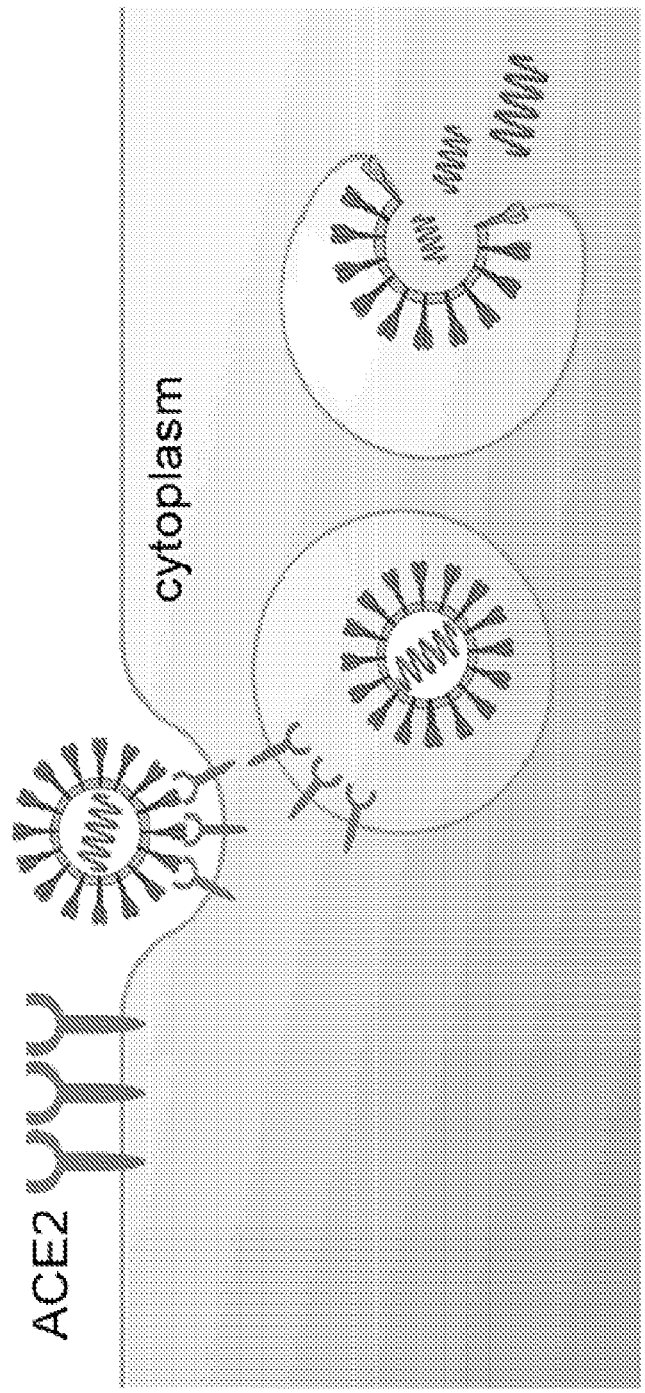

USE OF SALMETEROL AS AN ANTI-CORONAVIRAL AGENT

CROSS-REFERENCE TO RELATED APPLICATIONS

This application is the U.S. National Stage of PCT/US2021/028399 with international filing date Apr. 21, 2021 and which claims priority to U.S. Provisional Application No. 63/015,307 filed on Apr. 24, 2020. The content of each of the above-referenced applications is incorporated by reference herein in its entirety.

STATEMENT REGARDING FEDERALLY SPONSORED RESEARCH

This invention was made with government support under grant number R01 GM088790 awarded by the National Institutes of Health. The government has certain rights in this invention.

BACKGROUND

Coronaviruses (CoV) constitute a large family of positive-stranded, enveloped RNA viruses that infect a broad range of mammalian and avian species. The viruses cause primarily respiratory and enteric diseases. In the last two decades three new zoonotic CoVs have emerged to infect humans. The most recent to emerge is Severe Acute Respiratory Syndrome Coronavirus 2 (SARS-CoV-2) that continues to spread globally raising many scientific and public health questions and challenges. Currently, there are few effective treatments or therapeutics for coronavirus disease 2019 (COVID-19) caused by SARS-CoV-2. See, for example, Liu et al. ("Research and development on therapeutic agents and vaccines for COVID-19 and related human coronavirus diseases," ACS Central Science, 2020, 6, 315-331). Therefore, a need exists for COVID-19 therapeutics and treatments.

SUMMARY OF THE INVENTION

In a first aspect, provided herein is a method for treating coronavirus disease 2019 (COVID-19) in a subject in need thereof comprising administering to the subject a composition comprising a therapeutically effective amount of salmeterol or a pharmaceutically acceptable salt thereof, whereby one or more symptoms of COVID-19 are improved in the subject. In some embodiments, the pharmaceutically acceptable salt is salmeterol xinafoate. In some embodiments, the pharmaceutical composition is administered by inhalation. In some embodiments, the composition comprises a propellant. In some embodiments, the composition is administered topically to a mucosal tissue of the subject. In some embodiments, the mucosal tissue is nasal mucosa. In some embodiments, the composition is a suspension of powdered salmeterol or the pharmaceutically acceptable salt thereof. In some embodiments, the composition additionally comprises a steroid. In some embodiments, salmeterol or the pharmaceutically acceptable salt thereof is administered in a single or multiple doses of 10 µg to 100 µg per dose.

In a second aspect, provided herein is a method of preventing COVID-19 is a subject exposed to Severe Acute Respiratory Syndrome Coronavirus 2 (SARS-CoV-2) comprising administering to a subject exposed to SARS-CoV-2 a composition comprising a therapeutically effective amount of salmeterol or a pharmaceutically acceptable salt thereof, whereby one or more symptoms of COVID-19 is prevented. In some embodiments, the pharmaceutically acceptable salt is salmeterol xinafoate. In some embodiments, the composition is administered by inhalation. In some embodiments, the composition comprises a propellant. In some embodiments, the composition is administered topically to a mucosal tissue of the subject. In some embodiments, the mucosal tissue is nasal mucosa. In some embodiments, the composition is a suspension of powdered salmeterol or the pharmaceutically acceptable salt thereof. In some embodiments, the composition additionally comprises a steroid. In some embodiments, salmeterol or the pharmaceutically acceptable salt thereof is administered in a single or multiple doses of 10 µg to 100 µg per dose.

In a third aspect, provided herein is a method of inhibiting SARS-CoV-2 infectivity in a mammalian cell comprising administering to the mammalian cell a composition comprising a therapeutically effective amount of salmeterol or a pharmaceutically acceptable salt thereof, wherein salmeterol or the pharmaceutically acceptable salt thereof inhibits nicotinic acid adenine dinucleotide phosphate (NAADP) mediated $Ca^{2+}$ release and uptake of SARS-CoV-2 by two-pore channel (TPC) receptors of the mammalian cell. In some embodiments, the mammalian cell is a mucosal cell of a human subject exposed to SARS-CoV-2.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 6 shows MERS-COV spike protein colocalizes with endolysosomal ion channel positive structures. Huh7 cells were transfected with TPC1-GFP (top, green), TPC2-GFP (middle, green) and GFP-TRPML1 (bottom, green) and subsequently infected with MERS-pseudovirus (red). Cells were fixed, immunostained for MERS-COV spike protein (spike-AF555) and visualized by confocal microscopy. White boxes in overlay panel (right) show enlarged regions to assess colocalization between the red and green channel. Scale bars: 10 μm (left column) and 1 μm (inset, right).

INCORPORATION BY REFERENCE

Figure 1:
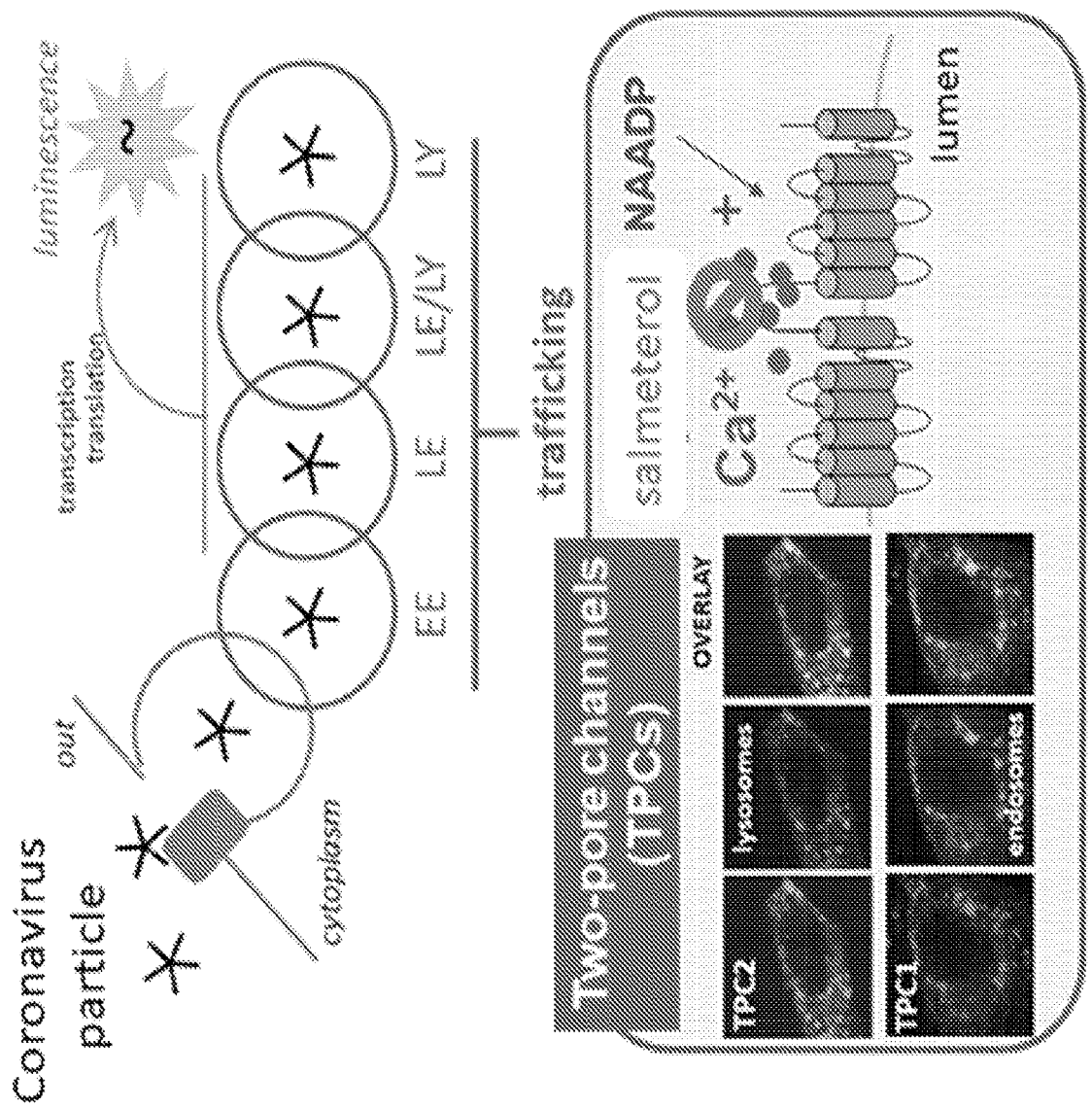
FIG. 1 shows TPCs regulate endolysosomal trafficking and microenvironment. Top, schematic of MERS-COV infection pathway, highlighting trafficking and processing events that occur within the endolysosomal system (blue). Replication is measured by luminescence in our particular assay system. Bottom, schematic of TPCs forming a NAADP-activated ion channel in acidic $Ca^{2+}$ stores. $Ca^{2+}$ release via TPCs is blocked by tetrandrine & fangchinoline, compounds that impair MERS infectivity (1-3). Images show immuno-localization of TPC1 (biased to endosomes) and TPC2 (lysosomal) together with organelle markers.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure describes methods for treating coronavirus disease 2019 (COVID-19), caused by Severe Acute Respiratory Syndrome Coronavirus 2 (SARS-CoV-2), by administration of salmeterol or a pharmaceutically acceptable salt thereof.

Salmeterol (IUPAC: (RS)-2-(hydroxymethyl)-4-{1-hydroxy-2-[6-(4-phenylbutoxy)hexylamino]ethyl}phenol), and pharmaceutically acceptable salts thereof, is approved by the U.S Food and Drug Administration for the treatment of asthma, chronic obstructive pulmonary disease (COPD) and bronchospasm. Salmeterol is a > that binds to both the active and exo sites of the beta-2 adrenergic receptor. Stimulation of the beta-2 adrenoceptor by salmeterol causes relaxation of bronchial smooth muscle, bronchodilation, and increased airflow.

Described herein is the action of salmeterol and pharmaceutically acceptable salts thereof to inhibit the cellular infectivity of a coronavirus in mammalian cells. Salmeterol is an inhibitor of two-pore channels (TPCs), which are a family of ion channels that reside within endosomes and lysosomes in cells that are activated by a potent $Ca^{2+}$-releasing secondary messenger, nicotinic acid adenine dinucleotide phosphate (NAADP). By inhibiting cellular TPCs, salmeterol inhibits NAADP evoked $Ca^{2+}$ release and uptake of SARS-CoV-2 viral particles. Modulation of NAADP-dependent $Ca^{2+}$ signaling by salmeterol is described in Gunaratne et al. ("A screening campaign in sea urchin egg homogenate as a platform for discovering modulators of NAADP-dependent $Ca^{2+}$ signaling in human cells," Cell Calcium, 2018, 75:42-52). The role of NAADP-dependent $Ca^{2+}$ signaling in MERS is described in Gunaratne et al. ("NAADP-dependent $Ca^{2+}$ signaling regulates Middle East respiratory syndrome-coronavirus pseudovirus translocation through the endolysosomal system," Cell Calcium, 2018, 75:30-41).

Suitable pharmaceutically acceptable salts of the salmeterol of use in the formulations of the present disclosure include acid addition salts such as for example sulphates, hydrochlorides and xinafoates (1-hydroxy-2-naphthoate), amine salts or alkali metal salts (e.g. sodium). In some embodiments, salmeterol will preferably be in the form of its xinafoate salt.

According to the methods of the present disclosure, salmeterol or a pharmaceutically acceptable salt thereof is administered to a subject in need thereof. Subjects in need of treatment include those already having or diagnosed with a disease or infection as described herein, or those who are at risk of developing a disease or infection as described herein.

A disease or infection of the present disclosure may include, but is not limited to, COVID-19, Middle East Respiratory Syndrome (MERS), SARS, a SARS-CoV-2 infection, an MERS coronavirus (MERS-COV) infection, or a SARS coronavirus (SARS-COV) infection.

As used herein, the terms "treat" and "treating" refers to therapeutic measures, wherein the object is to slow down (lessen) an undesired physiological change or pathological disorder resulting from a disease or infection as described herein. For purposes of this invention, treating the disease or infection includes, without limitation, alleviating one or more clinical indications, decreasing inflammation, reducing the severity of one or more clinical indications of the disease or infection, diminishing the extent of the condition, stabilizing the subject's disease or infection (i.e., not worsening), delay or slowing, halting, or reversing the disease or infection and bringing about partial or complete remission of the disease or infection. Treating the disease or infection also includes prolonging survival by days, weeks, months, or years as compared to prognosis if treated according to standard medical practice not incorporating treatment with salmeterol or a pharmaceutically acceptable salt thereof. For example, symptoms of COVID-19 include, but are not limited to, for example, fever, cough, shortness of breath or difficulty breathing, chills, repeated shaking with chills, muscle pain, headache, sore throat, new loss of taste or smell, trouble breathing, persistent pain or pressure in the chest, new confusion or inability to arouse, bluish lips or face, among others.

Subjects in need of treatment can include those already having or diagnosed with a disease or infection as described herein as well as those prone to, likely to develop, or suspected of having a disease or infection as described herein. Pre-treating or preventing a disease or infection according to a method of the present invention includes initiating the administration of a therapeutic (e.g., salmeterol or a pharmaceutically acceptable salt thereof) at a time prior to the appearance or existence of the disease or infection, or prior to the exposure of a subject to factors known to induce the disease or infection. Pre-treating the disorder is particularly applicable to subjects at risk of having or acquiring the disease. As used herein, the terms "prevent" and "preventing" refer to prophylactic or preventive measures intended to inhibit undesirable physiological changes or the development of a disorder or condition resulting from the disease or infection. In exemplary embodiments, preventing the disease or infection comprises initiating the administration of a therapeutic (e.g., salmeterol or a pharmaceutically acceptable salt thereof) at a time prior to the appearance or existence of the disease or infection such that the disease or infection, or its symptoms, pathological features, consequences, or adverse effects do not occur. In such cases, a method of the invention for preventing the disease or infection comprises administering salmeterol or a pharmaceutically acceptable salt thereof to a subject in need thereof prior to exposure of the subject to factors that influence the development of the disease or infection. In some embodiments, the subject is a human and the administration of salmeterol or a pharmaceutically acceptable salt thereof is intended for prevent advancement of COVID-19 following exposure of the human subject to SARS-CoV-2 or following diagnosis of SARS-CoV-2 infection in the subject.

As used herein, the terms "subject" or "patient" are used interchangeably and can encompass vertebrates including, without limitation, humans and mammals. However, advantageously, the subject or patient is a mammal such as a human, or a mammal such as a domesticated mammal, e.g., dog, cat, horse, and the like, or livestock, e.g., cow, sheep, pig, and the like. In some embodiments, the subject is a human. In some embodiments, the subject is s subject that has tested positive for SARS-CoV-2, or a subject that has been exposed to a person who tested positive for SARS-CoV-2.

As used herein, the phrase "in need thereof" indicates the state of the subject, wherein therapeutic or preventative measures are desirable. Such a state can include, but is not limited to, subjects having a disease or infection as described herein or a pathological symptom or feature associated with a disease or infection as described herein.

In some cases, a method of treating or preventing a disease or infection as described herein comprises administering a pharmaceutical composition comprising a therapeutically effective amount of salmeterol or a pharmaceutically acceptable salt thereof as a therapeutic agent (i.e., for therapeutic applications). As used herein, the term "pharmaceutical composition" refers to a chemical or biological composition suitable for administration to a mammal. Examples of compositions appropriate for such therapeutic applications include preparations for oral, topical, parenteral, subcutaneous, transdermal, intradermal, intramuscular, intraperitoneal, intraocular, intravenous (e.g., injectable), intraparenchymal, intrathecal, or intraarterial administration. In some cases, pharmaceutical compositions appropriate for therapeutic applications may be in admixture with one or more pharmaceutically acceptable excipients, diluents, or carriers such as sterile water, physiological saline, glucose or the like. For example, salmeterol or a pharmaceutically acceptable salt thereof can be administered to a subject as a pharmaceutical composition comprising an aerosol delivery vehicle.

Formulations may be designed or intended for oral, respiratory, rectal, nasal, topical or transmucosal (including buccal, sublingual, ocular, vaginal and rectal) and parenteral (including subcutaneous, intramuscular, intravenous, intradermal, intraperitoneal, intrathecal, intraocular intraparenchymal, intrathecal and epidural) administration. In some embodiments, the formulation may be a sterile suspension, emulsion, or aerosol. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal, intraparenchymal or intramuscular depot. In some cases, pharmaceutical compositions are lyophilized. In other cases, pharmaceutical compositions as provided herein contain auxiliary substances such as wetting or emulsifying agents, fillers, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

In some embodiments, the pharmaceutical formulation of salmeterol or a pharmaceutically acceptable salt thereof is a powder or an aerosol formulation for respiratory or oral administration by inhalation. A suitable aerosol formulation may include a propellant, for example a liquefied or compressed gas propellant. In some embodiments, the salmeterol or a pharmaceutically acceptable salt thereof is a powder suspended in a liquefied gas propellant. In some embodiments, the aerosol formulation includes a surfactant.

In some embodiments, the salmeterol or a pharmaceutically acceptable salt thereof is in the form of a particulate powder. The particle size of the particulate (e.g. micronised) powder should be such as to permit inhalation of substantially all of the salmeterol or a pharmaceutically acceptable salt thereof into the lungs upon administration of the aerosol formulation and will thus be less than 100 microns, desirably less than 20 microns, and preferably in the range 1-10 microns, e.g. 1-5 microns.

In some embodiments, the aerosol formulation density contains 0.005-10% w/w, 0.005-5% w/w, or 0.01-1.0% w/w, of salmeterol or a pharmaceutically acceptable salt thereof relative to the total weight of the aerosol formulation.

Suitable propellants fluorocarbon or hydrogen-containing chlorofluorocarbon or mixtures thereof having a sufficient vapour pressure to render them effective as propellants. In some embodiments, the propellant will be a non-solvent for salmeterol or a pharmaceutically acceptable salt thereof. Suitable propellants include, for example, $C_{1-4}$,hydrogen-containing chlorofluorocarbons such as $CH_2ClF$, $CCLF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$. In some embodiments, propellants are $C_{1-4}$hydrogen-containing fluorocarbons such as 1.1.1.2-tetrafluoroethane ($CF_3CH_2F$) and 1,1,1,2,3,3,3-heptafluoro-n-propane ($CF_1CHFCF_1$).

In some embodiments, the pharmaceutical formulation of salmeterol or a pharmaceutically acceptable salt thereof is an aqueous suspension suitable for topical application to the mucosa of the subject. In some embodiments, the aqueous suspension is administered topically to the nasal mucosa in the form of a nasal spray.

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, salmeterol or a pharmaceutically acceptable salt thereof may be optionally administered in combination with one or more additional active agents. Such active agents include anti-inflammatory, anti-cytokine, analgesic, antipyretic, antibiotic, and antiviral agents, as well as growth factors and agonists, antagonists, and modulators of immunoregulatory agents (e.g., TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). In some embodiments, the salmeterol or a pharmaceutically acceptable salt thereof may be administered in combination with a steroid. Any suitable combination of such active agents is also contemplated. When administered in combination with one or more active agents, salmeterol or a pharmaceutically acceptable salt thereof can be administered either simultaneously or sequentially with other active agents.

Therapeutically effective amounts of salmeterol or a pharmaceutically acceptable salt thereof are administered to a subject in need thereof. An effective dose or amount is an amount sufficient to effect a beneficial or desired clinical result. With regard to methods of the present invention, the effective dose or amount, which can be administered in one or more administrations, is the amount of salmeterol or a pharmaceutically acceptable salt thereof sufficient to elicit a therapeutic effect in a subject to whom it is administered. In some cases, an effective dose of salmeterol or a pharmaceutically acceptable salt thereof is about 1 µg to about 200 µg (e.g., 1 µg, 5 µg, 10 µg, 12 µg, 15 µg, 20 µg, 25 µg, 30 µg, 40 µg, 50 µg, 75 µg, 100 µg, 150 µg, or 200 µg). Effective amounts will be affected by various factors that modify the action of the extract upon administration and the subject's biological response to the extract, e.g., severity of COVID-19, type of coronavirus infection, the subject's age, sex, and diet, the severity of pulmonary inflammation, time of administration, and other clinical factors.

Suitable formulation and dosing strategies for administration of salmeterol or the pharmaceutically acceptable salt thereof are known and described in the art. See, for example, U.S. Pat. Nos. 7,090,831 and 6,303,103, each of which are incorporated herein by reference.

Therapeutically effective amounts for administration to a human subject can be determined in animal tests and any art-accepted methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the salmeterol or a pharmaceutically acceptable salt thereof. For example, dosage of the salmeterol or a pharmaceutically acceptable salt thereof for a particular subject with COVID-19 can be increased if the lower dose does not elicit a detectable or sufficient improvement in respiratory flow, mucus clearance, or inflammation. Conversely, the dosage can be decreased if the COVID-19 is treated or eliminated.

In some cases, therapeutically effective amounts of salmeterol or a pharmaceutically acceptable salt thereof can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, route of administration, and the nature of any concurrent therapy.

Following administration of salmeterol or a pharmaceutically acceptable salt thereof to an individual subject afflicted by, prone to, or likely to develop a disease or infection described herein, a clinical symptom or feature associated with the disease or infection is observed and assessed for a positive or negative change. For example, for methods of treating COVID-19 in a subject, positive or negative changes in the subject's respiratory flow, mucus clearance, and pulmonary inflammation during or following treatment may be determined by any measure known to those of skill in the art including, without limitation, spirometry metrics (e.g., serial 12-hour forced expiratory flow in 1 second ($FEV_1$) and morning/evening peak expiratory flow rate (PEFR), MRI scan, CT scan, and chest X-ray.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

EXAMPLES

Example 1: Identification of Salmeterol as a TPC Antagonist Treatment for COVID-19

Many pathogens pass through the organelles of the endolysosomal system ('acidic $Ca^{2+}$ stores') as part of their infective cycle. These include many viruses (MERS-COV, SARS-COV, SARS-CoV-2, Ebola, Zika virus, enterovirus A17, HIV, influenza), bacteria (e.g. *Mycobacterium*) and eukaryotic pathogens (*Toxoplasma, Plasmodium*). Many of these agents are responsible for serious clinical infections that often lack effective treatments. While it has long been recognized that crude manipulations of the endolysosomal system (e.g. lytic and lysomotropic agents) can impair the viability of these agents, it is unlikely that such 'blunt force trauma' of host cell organelles could realize a therapeutic approach owing to the anticipated host side effects.

For two single stranded RNA viruses, MERS-COV and Ebola, two recent papers have highlighted a novel approach to chemotherapy. In independent studies, MERS-COV (1,2) and Ebola (3) infectivity was shown to be reduced by drugs demonstrated to act as blockers of two-pore channels (TPCs). Two-pore channels are a recently discovered family of ion channels that reside within endosomes and lysosomes in cells ('acidic' $Ca^{2+}$ stores) that are activated by a potent $Ca^{2+}$-releasing second messenger, nicotinic acid adenine dinucleotide phosphate (NAADP, FIG. 1). Three pieces of experimental evidence hold high relevance:

First, in a paper published in Science, Sakurai et al. showed that the TPC antagonist tetrandrine (a benzylisoquinoline natural product) blocked Ebola infectivity both in vitro and using an in vivo mouse model (3). Subsequently, our work showed that fangchinoline (a related bisbenzylisoquinoline) impaired MERS-COV pseudovirus infectivity in human cell lines (1,2). Both these studies revealed that these agents act as TPC antagonists, blocking $Ca^{2+}$ release evoked by NAADP from 'acidic' organellar $Ca^{2+}$ stores of the endolysosomal system. The TPC blocker, tetrandrine, has very recently been shown to be effective against SARS-CoV-2 in human cells, evidencing the broad anti-coronaviral activity of TPC modulators (4).

Second, these pharmacological data were complemented by molecular approaches. RNAi of TPCs in human cell lines (but not other endolysosomal $Ca^{2+}$ channels, e.g. TRPML1 (1)), or knockout of TPCs in a mouse model (3), replicated the protective effect of these TPC blockers. Collectively these data show that block of $Ca^{2+}$ release via TPCs provides a deft approach to alter the endolysosomal milieu to prevent viral infectivity.

Third, using a reciprocal approach, an in silico datamining study from several anti-viral screens docked known 'hits' into models of TPC structures, revealing many antiviral agents act as effective TPC antagonists (5).

Mechanistically, inhibition of CoV infectivity occurred by a two-hit mechanism-first TPC blockade altered the luminal microenvironment preventing appropriate virus processing, and secondly TPC blockade prevented normal $Ca^{2+}$ release and thereby trafficking and fusion of subsets of endosomes and lysosomes used as viruses translocate through endolysosomes into the cytoplasm (1-3).

These recent data (1,2,4) underscore the scientific basis for our work: TPCs represent a novel target for impairing coronaviral infectivity. Consequently, identifying novel chemotypes that block TPC activity holds significance for discovering novel antiviral agents.

Based on these discoveries, we recently executed a miniaturized drug screen to identify novel inhibitors of TPC activity. This was assessed by screening for compounds that both inhibited (i) NAADP-evoked $Ca^{2+}$ release from endosomes and lysosomes and (ii) CoV infectivity (screened by examining inhibition of infectivity of a MERS pseudovirus).

The results of these activities, described below, identified salmeterol, as a top hit-able to inhibit both MERS infectivity and TPC activity. The anti-CoV of salmeterol has not previously been appreciated. As an FDA-approved therapy, salmeterol represents a candidate for repurposing through emergency use authorization to treat COVID-19.

Figure 2:
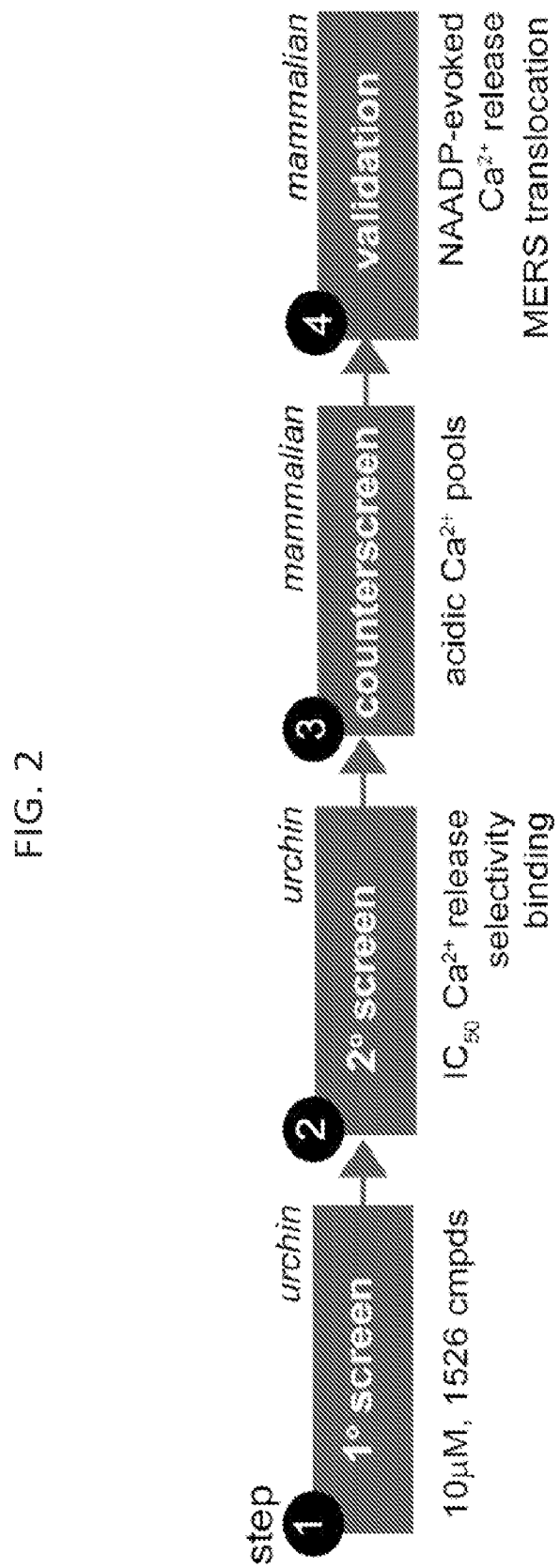
FIG. 2 shows the workflow for the drug screen to identify and validate inhibitors of CoV infectivity. Small molecule libraries (1534 compounds) were screened for inhibitors of NAADP evoked $Ca^{2+}$ release in sea urchin egg homogenate. Primary screen hits were validated and characterized prior to testing against $Ca^{2+}$ signals evoked by NAADP microinjection and MERS-COV cell entry in mammalian cells.
Figure 3:
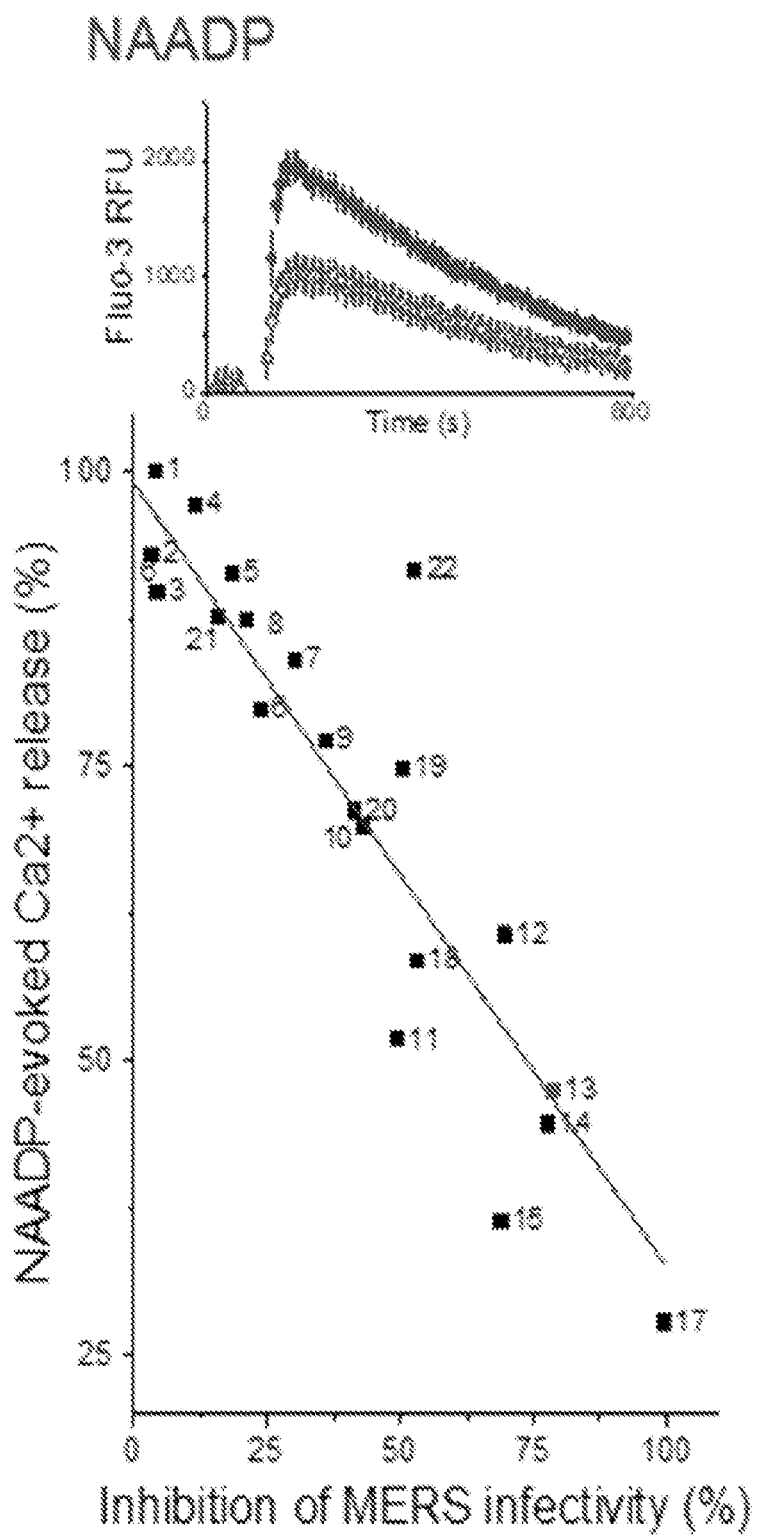
FIG. 3 shows drugs that inhibit NAADP-evoked $Ca^{2+}$ release block MERS infectivity. $Ca^{2+}$ release as resolved by fluo-3 fluorescence measurements. $Ca^{2+}$ liberation was measured in the absence (solid circles, top trace) or presence of fangchinoline (open circles, 10 µM) in response to NAADP (blue, 70 nM), IP3 (red, 200 nM) or cADPR (green, 100 nM). Data represent values from a minimum of three independent experiments and are expressed as mean±SEM. Correlation plots comparing the extent of inhibition of NAADP-(blue) IP3-(red) or cADPR-evoked $Ca^{2+}$ release (green) observed with individual ligands (10 µM) correlated with the extent of inhibition of MERS-COV translocation evoked by the same ligands (at the same concentration, 10 µM). None of these tested ligands evoked $Ca^{2+}$ release by themselves.
Figures 4A, 4B, 4C:
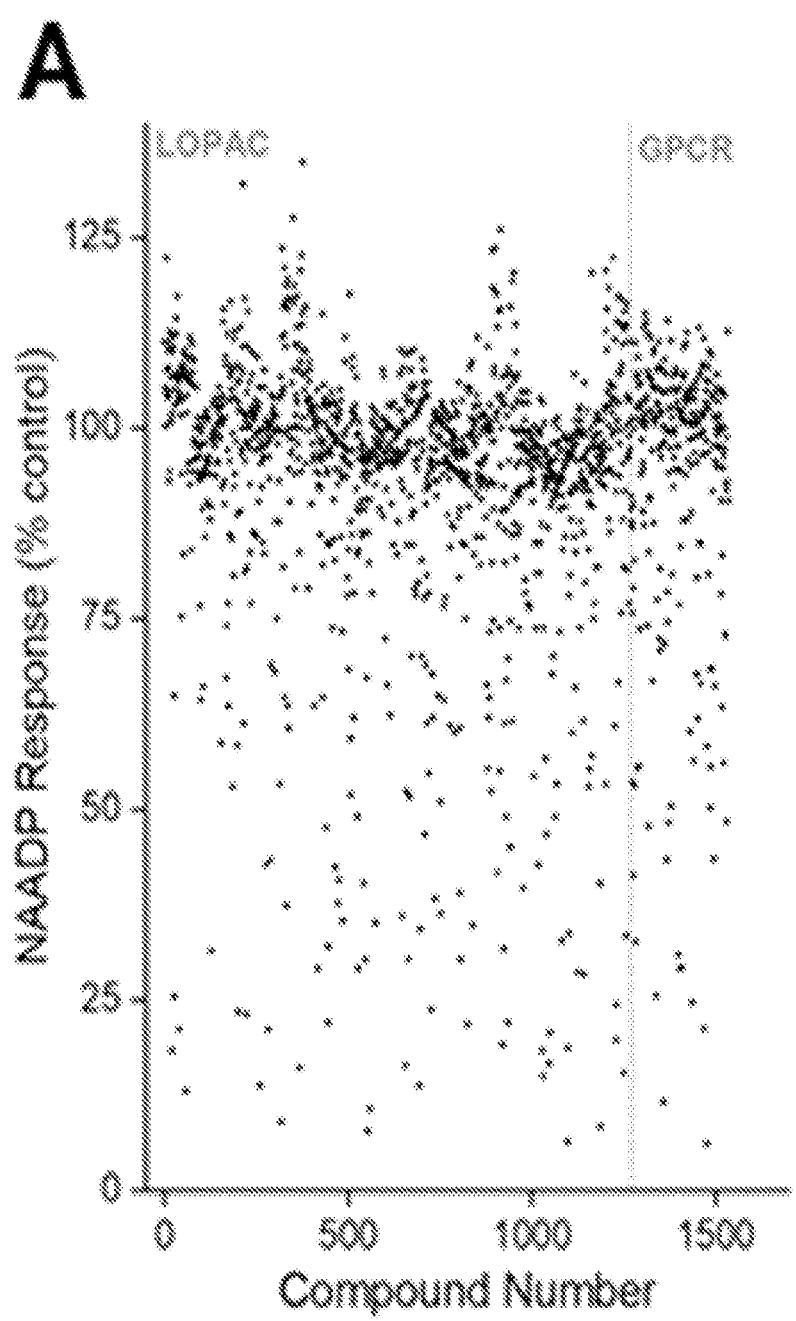
FIGS. 4A-4C show identification of top hits from the drug screen. (A) Scatter plot of average peak amplitude of NAADP-evoked $Ca^{2+}$ release in the presence of drug (25 μM) from LOPAC®1280 (left, numbered 1-1280) or Selleck (GPCR) compound library (right, numbered 1281-1534). (B) Results from both libraries were combined and compounds were ranked by amplitude of response from greatest inhibition (rank #1, left) to potentiation (rank #1534, right). The majority of compounds were in a range±25% of control response (shaded box). Compounds that exhibited >80% inhibition of NAADP-evoked $Ca^{2+}$ release were prioritized (red box) and selected for further characterization. (C) enlargement of red box to highlight the FDA-approved therapeutic, salmeterol which ranked #16/1534 compounds for TPC inhibition.
Figures 4A, 4B, 4C:
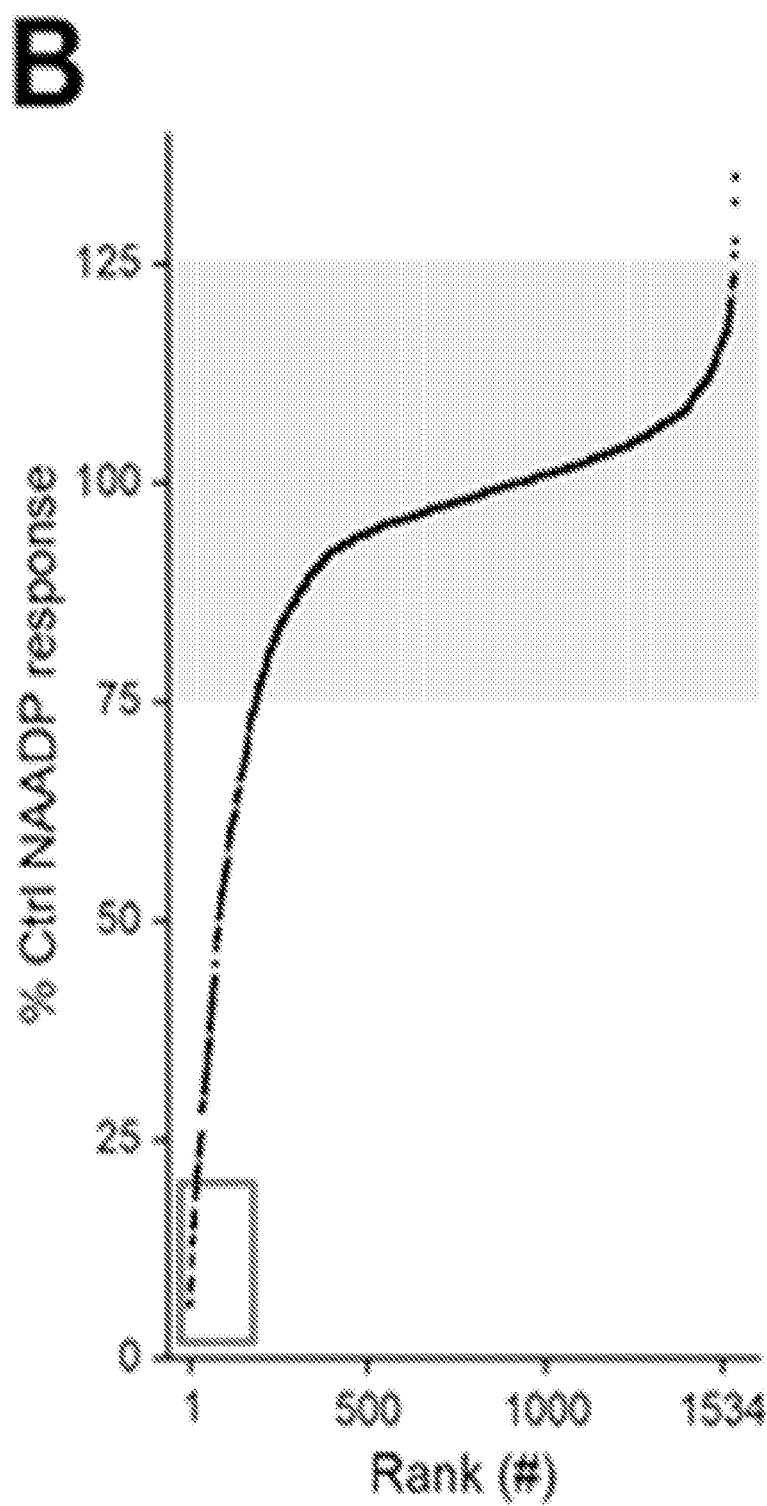
Figures 4A, 4B, 4C:
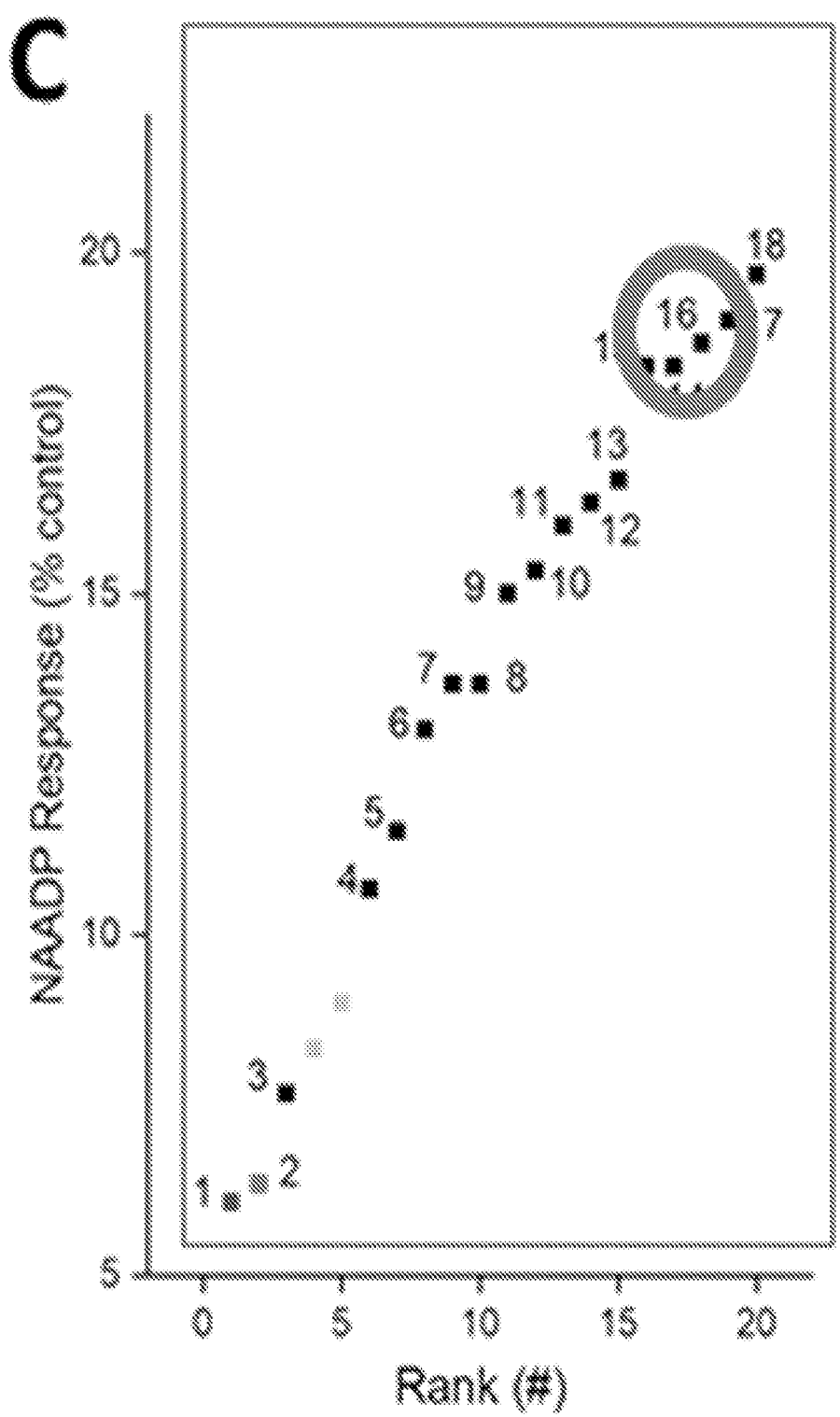
Figures 5A, 5B:
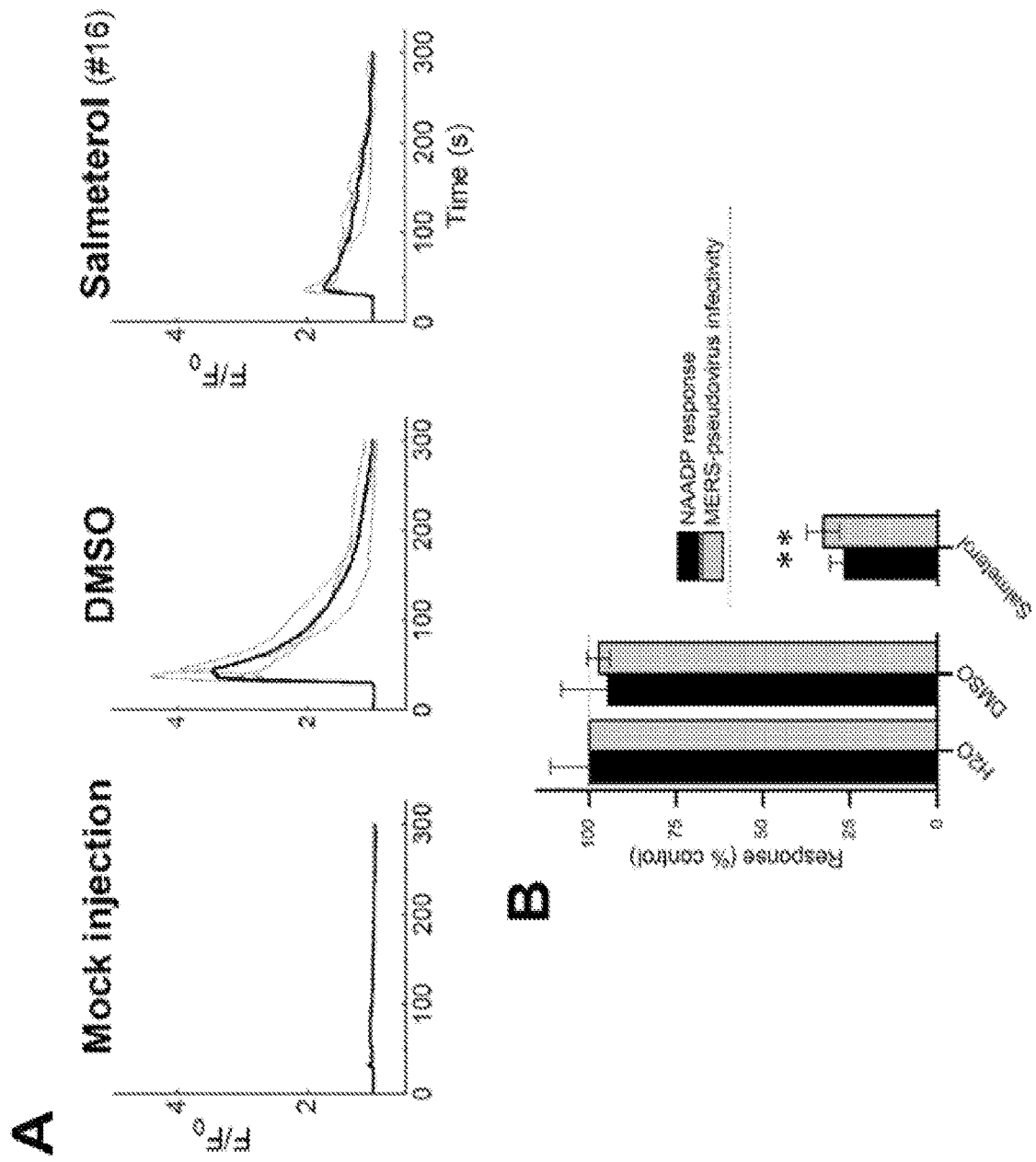
FIGS. 5A-5B show a validation of TPC inhibition and anti-coronaviral activity in mammalian cells. (A) $Ca^{2+}$ traces resolved by fluo-4 fluorescence in response to NAADP microinjection (100 nM pipette concentration) in U2OS cells treated with vehicle control, or salmeterol (10 μM, 10 min pretreatment). Individual traces shown in red, averaged response shown in black. (B) Quantification of peak amplitude of NAADP-evoked $Ca^{2+}$ transients in microinjected U2OS cells relative to control (black bars) following preincubation with indicated drugs as shown in (A). Grey bars report luciferase levels in a MERS-pseudovirus cell infection assay in Huh7 cells relative to controls ($H_2O$, DMSO) following treatment with the same panel of drugs (10 μM for 1 h prior to exposure to MERS-pseudovirus for a 5 h period). MERS-pseudovirus cell entry was detected 3 days post infection by measuring luciferase activity as described fully in the companion paper [25]. p-values: * p<0.05, ** p<0.01 relative to DMSO controls.
Figures 5A, 5B:
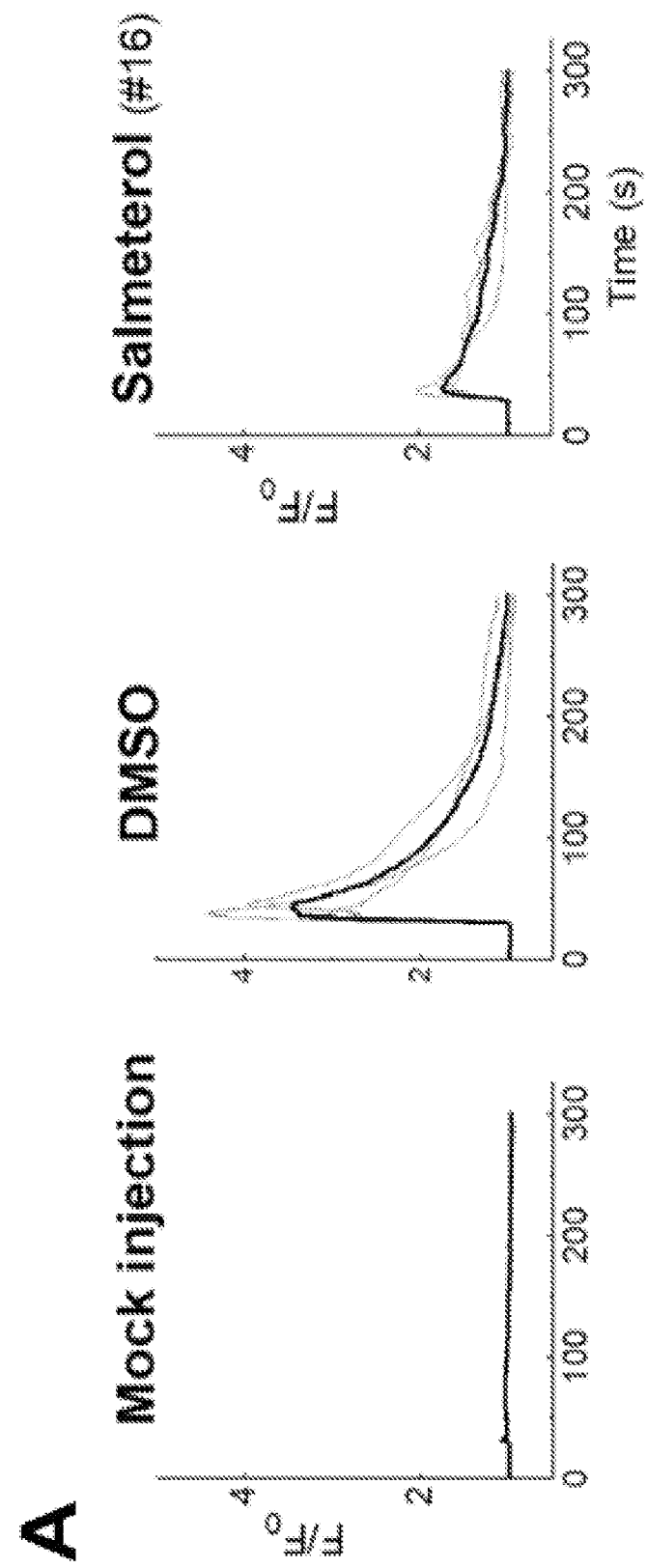
Figures 5A, 5B:
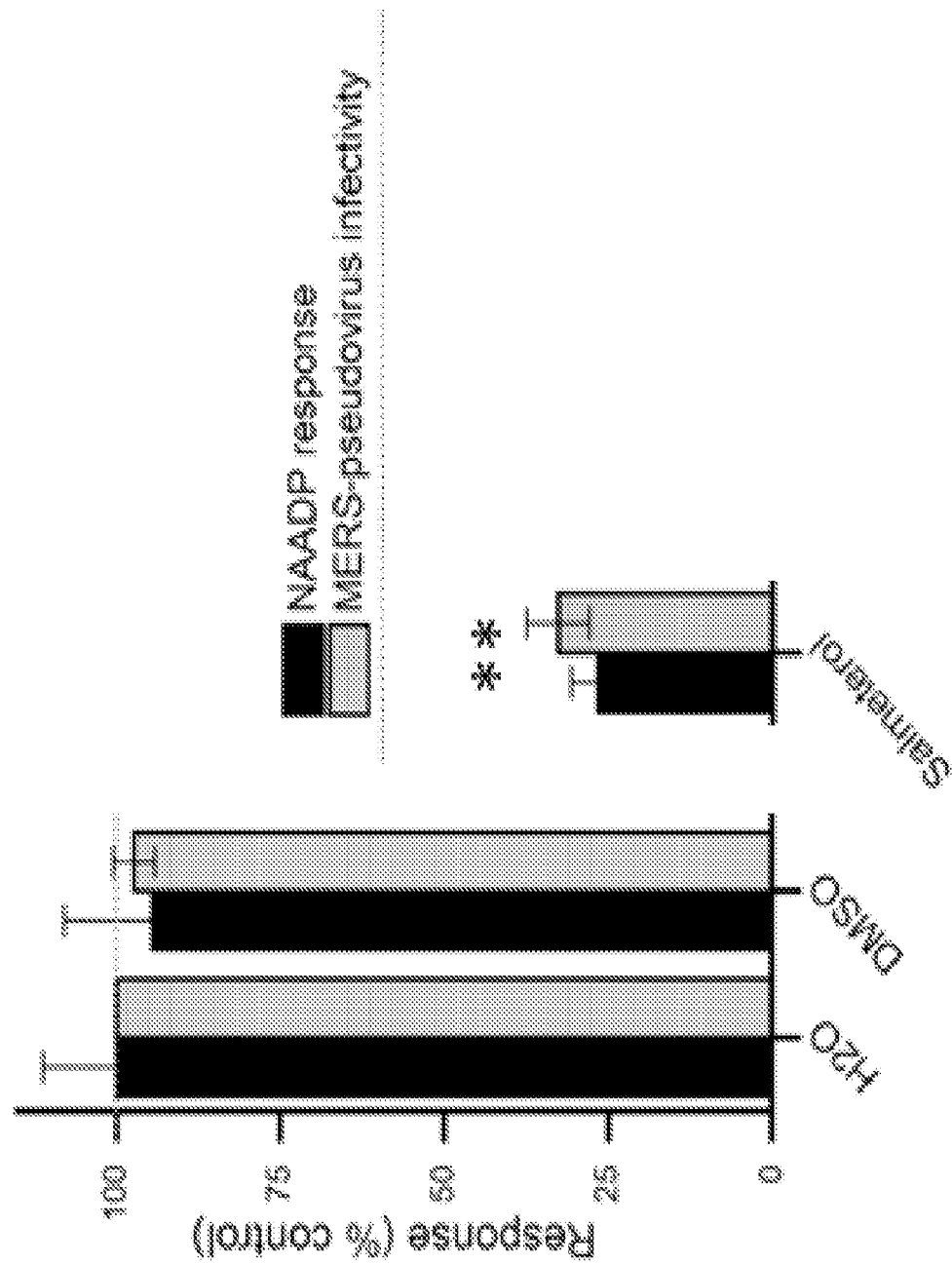

A rigorous screening pipeline for drugs that inhibit CoV-infectivity and NAADP-evoked $Ca^{2+}$ release was established. This pipeline encompassed primary, second screening and counter-screening activities for toxicity and off-target effects in human cells (FIG. 2). Experiments were performed to validate TPCs as novel anti-coronaviral targets. Inhibition of NAADP-evoked $Ca^{2+}$ release correlated with inhibition of coronaviral infectivity for a multiplicity of compounds (FIG. 3). Salmeterol was identified as the top hit in the drug screen that is a current FDA-approved therapeutic (FIGS. 4A-4C). Salmeterol was potent and penetrant in inhibition of MERS-COV infectivity in a pseudovirus translocation assay (FIGS. 5A-5B). TPC channels are present in organellar structures through which CoVs translocate, supporting the rigor of target identification (FIG. 6). TPC blockers inhibit SARS-COV 2 infectivity (4). There is therefore a high likelihood that compounds we have identified will show broad anti-CoV efficacy.

In addition to the unrecognized anti-CoV activity of salmeterol recently reported by us (6) and outlined above, salmeterol will likely afford additional symptomatic benefits in COVID-19 positive patients. Symptomatic benefits of salmeterol therapy will include (i) improved respiratory flow-COVID-19 is a disease of oxygen insufficiency, salmeterol improves patient lung function consistent with its use as an asthma long-term controller medication and salmeterol causes long-term improvements in various spirometry metrics including serial 12-hour forced expiratory flow in 1 second ($FEV_1$) and morning/evening peak expiratory flow rate (PEFR) (7-11); (ii) improved mucus clearance-salmeterol causes a rapid and prolonged increase in ciliary beat frequency which is predicted to be of benefit for removal of SARS-Cov-2 enhanced mucus deposition which impairs lung function (12); and (iii) anti-inflammatory activity-salmeterol exerts a potent and long-lasting inhibition of mast cell degranulation in the human lung, which may attenuate COVID-19 induced inflammatory lung damage, and salmeterol inhibits inflammatory responses mediated by neutrophils and mononuclear cells both in vitro and in vivo (13,14).

Additional benefits include; (i) effective targeting of lung tissue-salmeterol is delivered by inhalation, delivering high concentrations of antiviral agent into lung tissue which represents the core target tissue for SARS-CoV-2 pathology and patient lethality; and (ii) ease of use in out-patient settings-Existing FDA-approved salmeterol formulations are packaged as convenient inhalers that facilitate use in an out-patient setting, minimizing strain on clinic and hospital infrastructure. Inhalers are familiar to patients and easy to use.

Example 2: Effect of Salmeterol on Endolysosomal Viral Translocation

Figures 7A, 7B:
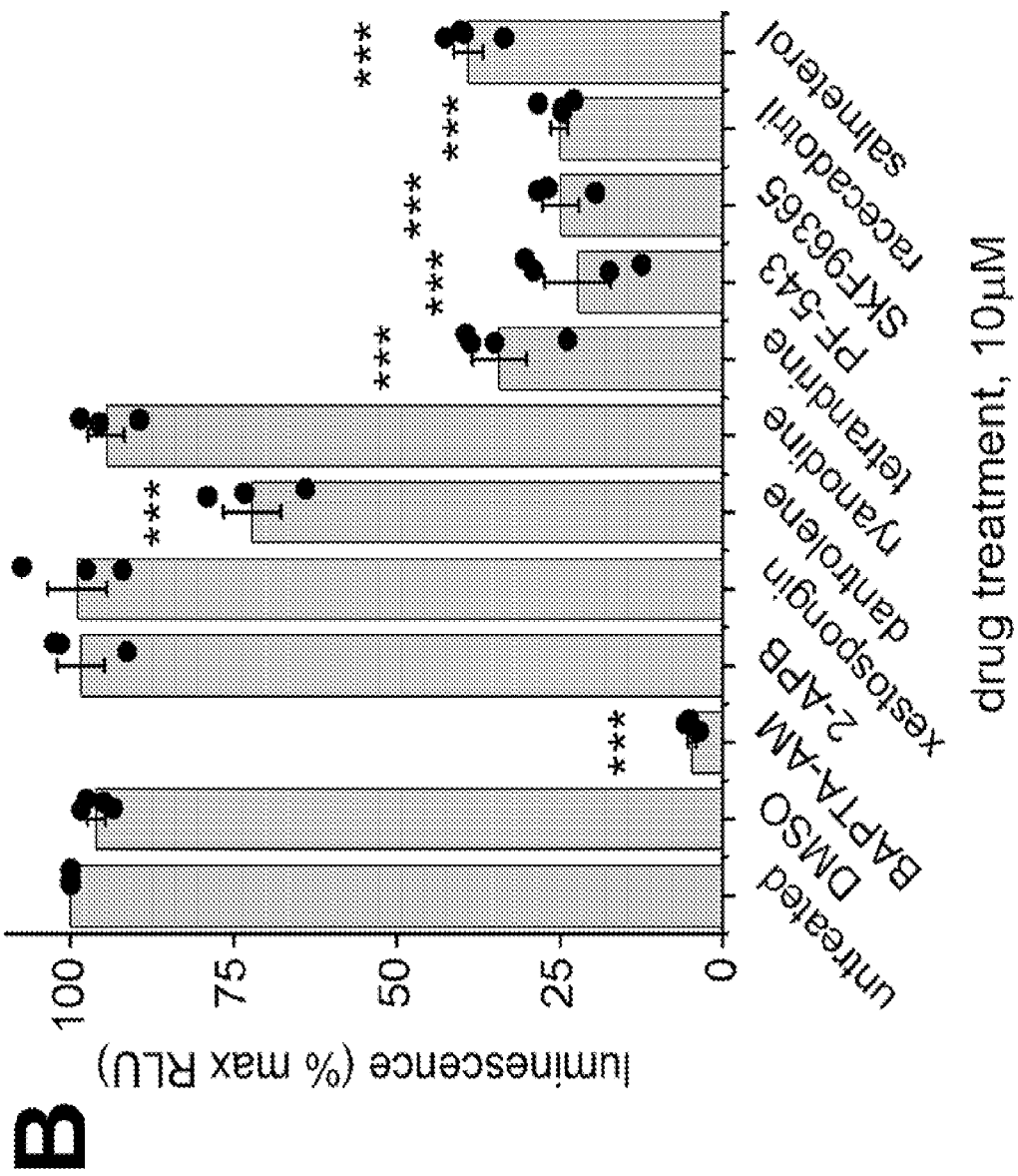
FIGS. 7A-7B demonstrate that salmeterol inhibits SARS-CoV-2 translocation through the endolysosomal system. (A) Schematic depiction of SARS-CoV-2 cell entry mediated by ACE2 internalization and translocation through acidic $Ca^{2+}$ stores. (B) Luciferase activity in cell lysates after transduction with a luciferase-encoding SARS-CoV-2 pseudovirus. HEK293 cells expressing ACE2 were transduced with SARS-CoV-2 pseudovirus in the presence of the indicated compound (10 μM). Drugs represent known inhibitors of IP3Rs (2-APB, xestospongin), RyRs (dantrolene, ryanodine), and salmeterol as well as others inhibitors of NAADP-evoked $Ca^{2+}$ release (tetrandrine, PF-543, SKF96365, racecadotril, salmeterol). Data represent results from n=3 independent assays, with values shown as mean±SEM. Statistical significance was assessed using a univariate regression model (*** P<0.005).

We analyzed the effects of salmeterol on the endolysosomal translocation of a SARS-CoV-2 pseudovirus (1). Viral translocation trafficking was monitored using a reporter assay (2-4) where the pseudovirus generates a luminescence signal after release into the cytoplasm, thereby reporting the efficiency of subcellular translocation events (ACE2 receptor binding, internalization, endolysosomal processing and transit, cytoplasmic release, FIG. 7A). First, we tested the effect of the $Ca^{2+}$ chelating agent BAPTA-AM, which resulted in nearly complete inhibition of SARS-CoV-2 pseudovirus infectivity, indicating that intracellular $Ca^{2+}$ signaling plays an essential role in SARS-CoV-2 cellular entry. Next, we analyzed the effects of previously screened inhibitors of NAADP-evoked $Ca^{2+}$ release, including salmeterol (FIG. 7B). Salmeterol (10 μM) caused a pronounced inhibition of SARS-CoV-2 pseudovirus infectivity. Drugs targeting IP3Rs (2-APB, xestospongin) or RyRs (ryanodine) had no effect.

References for Example 2

1. Gunaratne, G. S., Brailoiu, E., He, S., Unterwald, E. M., Patel, S., Slama, J. T., Walseth, T. F., and Marchant, J. S. (2021) Essential requirement for Jupiter Microtubule Associated Homolog 2 in NAADP-evoked $Ca^{2+}$ signaling and SARS-CoV-2 infectivity. *Science Signaling (in press)*
2. Gunaratne, G. S., Yang, Y., Li, F., Walseth, T. F., and Marchant, J. S. (2018) NAADP-dependent Ca (2+) signaling regulates Middle East respiratory syndrome-coronavirus pseudovirus translocation through the endolysosomal system. *Cell Calcium* 75, 30-41
3. Gunaratne, G. S., Johns, M. E., Hintz, H. M., Walseth, T. F., and Marchant, J. S. (2018) A screening campaign in sea urchin egg homogenate as a platform for discovering modulators of NAADP-dependent Ca (2+) signaling in human cells. *Cell Calcium* 75, 42-52
4. Shang, J., Wan, Y., Luo, C., Ye, G., Geng, Q., Auerbach, A., and Li, F. (2020) Cell entry mechanisms of SARS-CoV-2. *Proc. Natl. Acad. Sci. U.S.A.* 117, 11727-11734

We claim:

1. A method for treating coronavirus disease 2019 (COVID-19) in a subject in need thereof comprising administering to the subject a composition comprising a therapeutically effective amount of salmeterol or a pharmaceutically acceptable salt thereof, whereby one or more symptoms of COVID-19 are improved in the subject and wherein the composition is administered by inhalation.

2. The method of claim 1, wherein the pharmaceutically acceptable salt is salmeterol xinafoate.

3. The method of claim 1, wherein the composition comprises a propellant.

4. The method of claim 1, wherein the composition is administered to the nasal mucosal tissue of the subject.

5. The method of claim 4, wherein the composition is administered to the subject as a nasal spray.

6. The method of claim 1, wherein the composition is a suspension of powdered salmeterol or the pharmaceutically acceptable salt thereof.

7. The method of claim 1, wherein the composition additionally comprises a steroid.

8. The methods of claim 1, wherein salmeterol or the pharmaceutically acceptable salt thereof is administered in a single or multiple doses of 10 μg to 100 μg per dose.

9. A method of reducing the severity of COVID-19 in a subject exposed to Severe Acute Respiratory Syndrome Coronavirus 2 (SARS-CoV-2) comprising administering to a subject exposed to SARS-CoV-2 a composition comprising a therapeutically effective amount of salmeterol or a pharmaceutically acceptable salt thereof, whereby one or more symptoms of COVID-19 is treated and wherein the composition is administered by inhalation.

10. The method of claim 9, wherein the pharmaceutically acceptable salt is salmeterol xinafoate.

11. The method of claim 9, wherein the composition comprises a propellant.

12. The method of claim 9, wherein the composition is administered to the nasal mucosal tissue of the subject.

13. The method of claim 12, wherein the composition is administered to the subject as a nasal spray.

14. The method of claim 9, wherein the composition is a suspension of powdered salmeterol or the pharmaceutically acceptable salt thereof.

15. The method of claim 9, wherein the composition additionally comprises a steroid.

16. The method of claim 9, wherein salmeterol or the pharmaceutically acceptable salt thereof is administered in a single or multiple doses of 10 µg to 100 µg per dose.

17. A method of inhibiting SARS-CoV-2 infectivity in a mammalian cell comprising administering to the mammalian cell a composition comprising a therapeutically effective amount of salmeterol or a pharmaceutically acceptable salt thereof, wherein salmeterol or the pharmaceutically acceptable salt thereof inhibits nicotinic acid adenine dinucleotide phosphate (NAADP) mediated $Ca^{2+}$ release and uptake of SARS-CoV-2 by two-pore channel (TPC) receptors of the mammalian cell and wherein the composition is administered by inhalation.

18. The method of claim 17, wherein the mammalian cell is a nasal mucosal cell of a human subject exposed to SARS-CoV-2.

* * * * *

UNITED STATES PATENT AND TRADEMARK OFFICE
CERTIFICATE OF CORRECTION

| | | |
|---|---|---|
| PATENT NO. | : 12,329,727 B2 | Page 1 of 1 |
| APPLICATION NO. | : 17/920611 | |
| DATED | : June 17, 2025 | |
| INVENTOR(S) | : Jonathan Stephen Marchant et al. | |

It is certified that error appears in the above-identified patent and that said Letters Patent is hereby corrected as shown below:

In the Specification

Column 7, Line 3, "propellants fluorocarcon" should be --propellants include any fluorocarcon--.

Column 7, Line 11, "$C_{14}$hydrogen-containing" should be --$C_{1-4}$hydrogen-containing--.

Signed and Sealed this
Twenty-sixth Day of August, 2025

Coke Morgan Stewart
*Acting Director of the United States Patent and Trademark Office*